United States Patent
Hielscher et al.

(10) Patent No.: US 12,156,715 B2
(45) Date of Patent: Dec. 3, 2024

(54) FLEXIBLE OPTICAL IMAGING BANDS AND OPTICAL IMAGING METHODS FOR THE DIAGNOSIS AND MONITORING OF SYSTEMIC LUPUS ERYTHEMATOSUS IN FINGER JOINTS

(71) Applicant: The Trustees of Columbia University in the City of New York, New York, NY (US)

(72) Inventors: Andreas H. Hielscher, Brooklyn, NY (US); Alessandro Marone, New York, NY (US); Ioannis Kymissis, New York, NY (US); Youngwan Kim, New York, NY (US); Anca D. Askanase, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 17/230,268

(22) Filed: Apr. 14, 2021

(65) Prior Publication Data
US 2021/0228088 A1    Jul. 29, 2021

Related U.S. Application Data

(63) Continuation of application No. PCT/US2019/056869, filed on Oct. 18, 2019.
(Continued)

(51) Int. Cl.
*A61B 5/00* (2006.01)
*A61B 5/026* (2006.01)

(52) U.S. Cl.
CPC .......... *A61B 5/0082* (2013.01); *A61B 5/0261* (2013.01); *A61B 5/41* (2013.01);
(Continued)

(58) Field of Classification Search
None
See application file for complete search history.

(56) References Cited

U.S. PATENT DOCUMENTS 4,407,290 A * 10/1983 Wilber ............... G01N 21/3151
356/41
5,623,933 A *  4/1997 Amano .............. A61B 5/02007
600/500

(Continued)

FOREIGN PATENT DOCUMENTS

WO      2017189376 A1   11/2017

OTHER PUBLICATIONS

Nassef et al., "Microparticles (CD146) and Arterial Stiffness Versus Carotid Intima Media Thickness as an Early Predictors of Vascular Affection in Systemic Lupus Patients", Arch Rheumatol, vol. 31, Issue 1, pp. 31-40, 2016. (Year: 2016).*
(Continued)

*Primary Examiner* — Katherine L Fernandez
(74) *Attorney, Agent, or Firm* — Potomac Law Group, PLLC

(57) ABSTRACT

Systemic lupus erythematosus (SLE) can be diagnosed by affixing a plurality of light sources and a plurality of light detectors against the subject's body near a joint, and sequentially transmitting light from each of the plurality of light sources into the subject's body. Signals are acquired from each of the plurality of light detectors. The rise time of the acquired signals that occurs in response to an inflation of a pressure cuff is determined, and an indication of whether the joint is affected by SLE is made based on the determined rise time. In some embodiments, a plateau time of the acquired signals is also acquired, and the indication of whether the joint is affected by SLE is made based on the determined rise time and the determined plateau time.

15 Claims, 7 Drawing Sheets

Related U.S. Application Data

(60) Provisional application No. 62/747,728, filed on Oct. 19, 2018.

(52) U.S. Cl.
CPC .......... *A61B 5/6826* (2013.01); *A61B 5/6831* (2013.01); *A61B 5/6843* (2013.01); *A61B 5/7235* (2013.01); *A61B 2562/0238* (2013.01); *A61B 2562/043* (2013.01)

(56) References Cited

U.S. PATENT DOCUMENTS

| | | | |
|---|---|---|---|
| 2002/0165440 A1* | 11/2002 | Mason | A61B 5/6838 600/344 |
| 2009/0182204 A1 | 7/2009 | Semler et al. | |
| 2010/0324384 A1* | 12/2010 | Moon | A61B 5/6838 600/323 |
| 2011/0028808 A1 | 2/2011 | Kuratsune et al. | |
| 2015/0150458 A1 | 6/2015 | Hielscher et al. | |
| 2016/0360974 A1* | 12/2016 | Lange | A61B 5/349 |
| 2017/0296104 A1* | 10/2017 | Ryan | G16H 50/30 |
| 2019/0082982 A1* | 3/2019 | Li | A61B 5/02141 |
| 2021/0037932 A1* | 2/2021 | Min | A44C 9/0023 |

OTHER PUBLICATIONS

Elgendi, "On the Analysis of Fingertip Photoplethysmogram Signals", Current Cardiology Reviews, vol. 8, pp. 14-25, 2012. (Year: 2012).*

ThoracicKey, "Noninvasive Diagnosis of Upper Extremity Arterial Disease", online: https://thoracickey.com/noninvasive-diagnosis-of-upper-extremity-arterial-disease-2/, available on Feb. 26, 2017, accessed on Dec. 4, 2021. (Year: 2017).*

Danias et al., "Diagnosing SLE Arthritis with Dynamic Diffuse Optical Spectroscopy,", Arthritis and Rheumatology, Sep. 1, 2018, vol. 70, No. Supplement 9, Abstract. (Year: 2018).*

Lasker et al., "Dynamic optical imaging of vascular and metabolic reactivity in rheumatoid joints", Journal of Biomedical Optics, vol. 12, Issue 5, pp. 1-13; Sep./Oct. 2007. (Year: 2007).*

Ahmed et al., "Discrete cosine transform," IEEE Trans Comput., No. January, pp. 90-93, 1974.

Boas et al., "Diffuse optical imaging of brain activation: Approaches to optimizing image sensitivity, resolution, and accuracy," NeuroImage, vol. 23, No. Suppl. 1, pp. S275-S288, Nov. 2004.

Di Leo et al., "Optical imaging of the breast: Basic principles and clinical applications," American Journal of Roentgenology, vol. 209, No. 1, pp. 230-238, Jul. 2017.

Durduran et al., "Diffuse optics for tissue monitoring and tomography," Reports on Progress in Physics, Jun. 2, 2010, 076701, vol. 73(7), (43 pages).

Evans, "Peering inside the mind: Imaging brain activity with advanced diffuse optical tomography," Science Translational Medicine, vol. 8, No. 360, p. 360ec162, Oct. 2016 (Abstract).

Flexman et al., "Digital optical tomography system for dynamic breast imaging," Journal of Biomedical Optics, Jul. 1, 2011, vol. 16(7), p. 076014-1-076014-16.

Hielscher et al., "Evolution strategies for optical tomographic characterization of homogeneous media," Optics express, vol. 7, No. 13, pp. 507-518, 2000.

Hielscher, et al., "Frequency-Domain Optical Tomographic Imaging of Arthritic Finger Joints", Medical Imagining, IEEE Transactions, vol. 30, Issue 10, pp. 1725-1736, Oct. 2011.

Ioannou et al., "Hemodynamics induced after acute reduction of proximal thoracic aorta compliance," European Journal Vascular and Endovascular Surgery, vol. 26, No. 2, pp. 195-204, 2003.

Khalil et al., "Dynamic diffuse optical tomography imaging of peripheral artery disease," Biomedical Optics Express, vol. 3, No. 9, p. 2288, Sep. 2012.

Kim et al., "PDE-constrained multispectral imaging of tissue chromophores with the equation of radiative transfer," Biomedical Optics Express, Oct. 1, 2010, vol. 1(3), pp. 812-824.

Kim et al., "A PDE-constrained SQP algorithm for optical tomography based on the frequency-domain equation of radiative transfer", Inverse problems, Nov. 24, 2008, vol. 25(1), 015010 (20 pp.).

Koutsokeras et al., "Systemic lupus erythematosus: lupus nephritis," Nature Reviews Drug Delivery, vol. 13, No. 3, pp. 173-174, 2014.

La Paglia et al., "One year in review 2017: systems lupus erythematosus," Clin. Exp. Rheumatol., vol. 34, No. 4, pp. 551-561, 2017.

Lasker et al., "Dynamic optical imaging of vascular and metabolic reactivity in rheumatoid joints," Journal of Biomedical Optics, Sep./Oct. 2007, vol. 12(5), pp. 052001-1-052001-13.

Li et al., "A Comprehensive Review of Immune-Mediated Dermatopathology in Systemic Lupus Erythematosus," Journal of Autoimmunity, vol. 93, pp. 1-15, 2018 (Abstract).

Lisnevskaia et al., "Systemic Lupus Erythematosus," The Lancet, vol. 384, No. 9957, pp. 1878-1888, Nov. 2014.

Montejo et al., "Computer-aided diagnosis of rheumatoid arthritis with optical tomography, Part 1: feature extraction," Journal of Biomedical Optics, vol. 18, No. 7, p. 076002, 2013.

Montejo et al., "Computer-aided diagnosis of rheumatoid arthritis with optical tomography, Part 2: image classification," Journal of Biomedical Optics, vol. 18, No. 7, p. 076002, 2013.

Teng et al., "Wearable near-infrared optical probe for continuous monitoring during breast cancer neoadjuvant chemotherapy infusions," Journal of Biomedical Optics, vol. 22, No. 1, p. 014001, 2017.

Tromberg et al., "Assessing the future of diffuse optical imaging technologies for breast cancer management," Medical Physics, Jun. 1, 2008, vol. 35(6), pp. 2443-2451.

Yucel et al., "Functional Near Infrared Spectroscopy: Enabling routine functional brain imaging," Current Opinion in Biomedical Engineering, vol. 4, pp. 78-86, 2017.

Hielscher et al., "Dynamic Vascular Optical Tomographic Imaging for Peripheral Artery Disease and Breast Cancer," Neurophontonics and Biomedical Spectroscopy, Chapter 14, pp. 353-400, 2019.

International Search Report and Written Opinion mailed Jan. 10, 2020 for International Patent Application No. PCT/US2019/056869.

Danias et al., "Diagnosing SLE Arthritis with Dynamic Diffuse Optical Spectroscopy," Arthritis and Rheumatology, Sep. 1, 2018, vol. 70, No. Supplement 9, pp. 840-842.

Hielscher et al., "Near-infrared diffuse optical tomography", Disease Markers, (Jan. 1, 2002), vol. 18(5-6), pp. 313-337.

Supplementary European Search Report dated Jun. 30, 2022 for European Patent Application No. 19874377.5.

\* cited by examiner

FLEXIBLE OPTICAL IMAGING BANDS AND OPTICAL IMAGING METHODS FOR THE DIAGNOSIS AND MONITORING OF SYSTEMIC LUPUS ERYTHEMATOSUS IN FINGER JOINTS

CROSS REFERENCE TO RELATED APPLICATIONS

This Application is a continuation of International Application PCT/US2019/056869, filed Oct. 18, 2019, which claims the benefit of U.S. Provisional Application No. 62/747,728, filed Oct. 19, 2018, both of which are incorporated herein by reference in their entirety.

BACKGROUND

It is estimated that in the USA 1.5 million people suffer from systemic lupus erythematosus (SLE) arthritis, and 90% of these are women. There are approximately 16,000 new cases per year. Worldwide prevalence of SLE is estimated to be as great as 150 per 100,000 individuals, resulting in at least 5 million lupus patients worldwide. SLE is a serious, debilitating autoimmune disease that affects various organs and body systems and often involves joints. More than 90 percent of those affected will experience joint pain, stiffness and swelling at some time during the course of their illness. There is currently no cure for SLE. It is difficult to both diagnose and estimate the severity of lupus, because signs and symptoms vary considerably from person to person and there is no single diagnostic test for it. SLE arthritis is also difficult to evaluate because of the sometimes-evanescent nature of the symptoms and limitations of physical exams and imaging studies.

SUMMARY OF THE INVENTION

One aspect of the invention is directed to a first imaging system. The first imaging system comprises a flexible substrate and a plurality of LEDs positioned on the flexible substrate at intervals along the flexible substrate. The LEDs are positioned with respect to the flexible substrate to couple light into a finger of a subject. The first imaging system also comprises a plurality of photodetectors positioned on the flexible substrate at intervals along the flexible substrate. The LEDs are positioned with respect to the flexible substrate to detect light emanating from the finger. The first imaging system also comprises a controller; and a plurality of LED drivers configured to selectively illuminate each of the LEDs in response to receipt of a command from the controller. The controller accepts an output from each the photodetectors, and determines, from each output from each of the photodetectors, a level of light absorption or transmission within the finger.

In some embodiments of the first imaging system, the plurality of LEDs and the plurality of photodetectors are arranged in a plurality of modules, with each of the modules including at least one LED and at least one photodetector. In some embodiments of the first imaging system, the plurality of LEDs emit light with a wavelength between 500 and 560 nm. In some embodiments of the first imaging system, the flexible substrate comprises a flex circuit. In some embodiments of the first imaging system, the flexible substrate comprises a polyimide layer with a plurality of conductive traces disposed on the polyimide layer.

Some embodiments of the first imaging system further comprise a plurality of transimpedance amplifiers, and each of the transimpedance amplifiers is configured to amplify an output of a respective one of the photodetectors. Optionally, these embodiments may further comprise an analog-to-digital converter configured to digitize outputs of the transimpedance amplifiers and forward corresponding data to the controller.

Another aspect of the invention is directed to a first method of diagnosing systemic lupus erythematosus (SLE) in a subject. The first method comprises (a) affixing a plurality of light sources and a plurality of light detectors against the subject's body near a joint; and (b) sequentially transmitting light from each of the plurality of light sources into the subject's body. The first method also comprises (c) acquiring signals from each of the plurality of light detectors. The signals represent an amount of light that reaches each of the plurality of light detectors during a time when each of the plurality of light sources is transmitting light into the subject's body. The first method also comprises repeating steps (b) and (c) at a rate that is sufficiently high to determine a rise time and a plateau time of the acquired signals between a start time and a stop time. The first method also comprises determining a rise time of the acquired signals that occurs in response to an inflation of a pressure cuff. The inflation of the pressure cuff occurs between the start time and the stop time. The first method also comprises (f) outputting an indication of whether the joint is affected by SLE based on the determined rise time.

Some instances of the first method further comprise determining a plateau time of the acquired signals that occurs in response to the inflation of a pressure cuff, and in these instances step (f) is also based on the determined plateau time. In some of these instances, step (f) comprises outputting an indication that the joint is likely affected by SLE when the rise time is short and the plateau time is long. Alternatively, step (f) may comprise outputting an indication that the joint is likely not affected by SLE when the rise time is long and the plateau time is short.

In some instances of the first method, step (f) comprises outputting an indication that the joint is likely affected by SLE when the rise time is less than 20 seconds. In some instances of the first method, step (f) comprises outputting an indication that the joint is likely not affected by SLE when the rise time is more than 40 seconds.

In some instances of the first method, the transmitted light has a wavelength between 500 and 560 nm. in some of these instances, the pressure cuff is inflated to between 30 and 50 mmHg. In some instances of the first method, the rate is at least once per two seconds. In some instances of the first method, the stop time is at least 60 seconds after the start time. In some instances of the first method, the plurality of light sources and the plurality of light detectors are held against the subject's body near the joint using a flexible substrate.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Dynamic diffuse optical spectroscopy (dDOS) can be used to assess changes in light absorption through tissues during transient venous occlusion. The optical signal reflects changes in blood perfusion and has diagnostic value for SLE arthritis.

This application describes a system of flexible optical imaging bands that can be used to diagnose SLE and assess the effects of SLE on finger joints, and methods of using those optical imaging bands.

Figure 1:
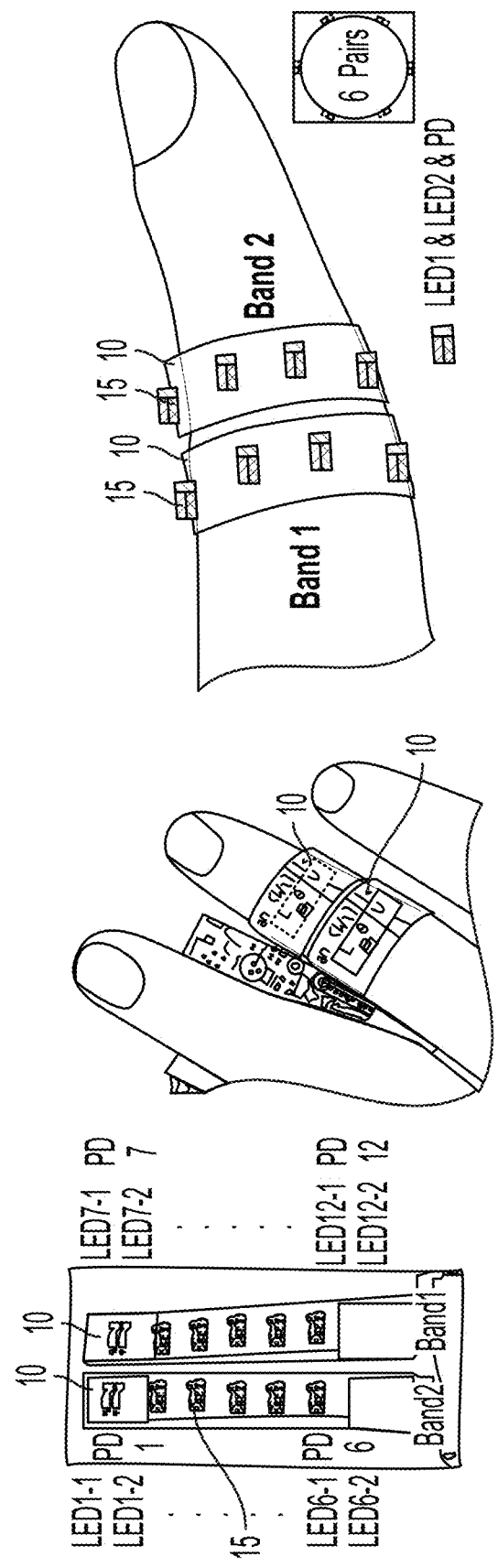
FIG. 1A depicts a set of two flexible imaging bands used for detecting SLE.
FIG. 1B depicts the imaging bands in position for use on a subject's fingers.
FIG. 1C is a schematic depiction of the imaging bands' positioning on a finger.

FIG. 1A depicts a set of two of these flexible imaging bands 10 before those imaging bands have been positioned on a subject's finger. Each of the imaging bands 10 is flexible and has a plurality of modules 15 spaced apart along the flexible imaging band 10. In the illustrated embodiment, each of the imaging bands 10 has six modules 15. As explained below, each of these modules 15 includes at least one light emitter (e.g., LED(s)) and at least one photodetector (e.g. photodiode(s)). In some preferred embodiments, the imaging bands 10 have a flexible form factor that supports conformal attachment on any body surface, especially wrapping around fingers.

FIG. 1B depicts a set of two imaging bands 10 in position for use on a subject's fingers. One of the imaging bands 10 is positioned on the distal side of the joint being examined, and the other imaging band 10 is positioned on the proximal side of the joint being examined (i.e., the same side as the heart).

FIG. 1C is a schematic depiction of the imaging bands' 10 positioning on a finger mesh, and shows the position of the various light emitters and photodetectors incorporated within the modules 15 of the imaging bands 10 with respect to the finger.

The substrate of each imaging band 10 is flexible, and may be made, for example of a polyimide substrate. In some preferred embodiments, the substrate of the imaging band 10 is a flex circuit. Each of the modules 15 includes surface mount optical components such as light emitting diodes (LEDs) and photodetectors (PDs) positioned on and operatively connected to a copper-patterned polyimide substrate. Each of the modules 15 includes at least one LED and at least one photodetector.

In the embodiment illustrated in FIGS. 1A-1C, there are six modules 15 in each imaging band 10. In some embodiments, each module 15 has a plurality of light emitters that operate at different wavelengths. For example, three LEDs at wavelengths of 530, 655, 940 nm may be used. A suitable power level for these LEDs is 2 mW. In some embodiments, the light detector on each of the modules 15 is a 1.7-mm$^2$ Si photodiode. Alternative photodetectors may also be used.

In the embodiment depicted in FIGS. 1A-1C, two imaging bands 10 are positioned around each joint of the subject. But in alternative embodiments, a different number of imaging bands 10 may be positioned around each joint (e.g., only a single band). The modules 15 on each of the imaging bands 10 are distributed at different positions along the length of the band. FIG. 1B shows two imaging bands 10 wrapped around the peripheral proximal interphalangeal (PIP) finger joint conformally. In FIG. 1C, the schematic of the imaging bands 10 around the finger mesh shows the location of the modules 15 (and the components included therein).

Note that while FIG. 1A depicts bands 10 that have six modules 15 per band, a different number of modules 15 could be provided on each band (e.g., between three and eight. In some embodiments, four modules are provided on each band). In some preferred embodiments, the individual light sources on each of the modules 15 are turned on and off one at a time by the system controller, and all photodetectors detect intensities of transmitted and reflected lights at different locations. The detected light, after traveling through tissue in the subject's body (e.g., tissue in the subject's finger), is measured and analyzed. In some embodiments, four modules 15 are spaced about 1.5 cm apart from each other, with the modules located on the top, bottom, and both sides of the finger, respectively.

Figure 2:
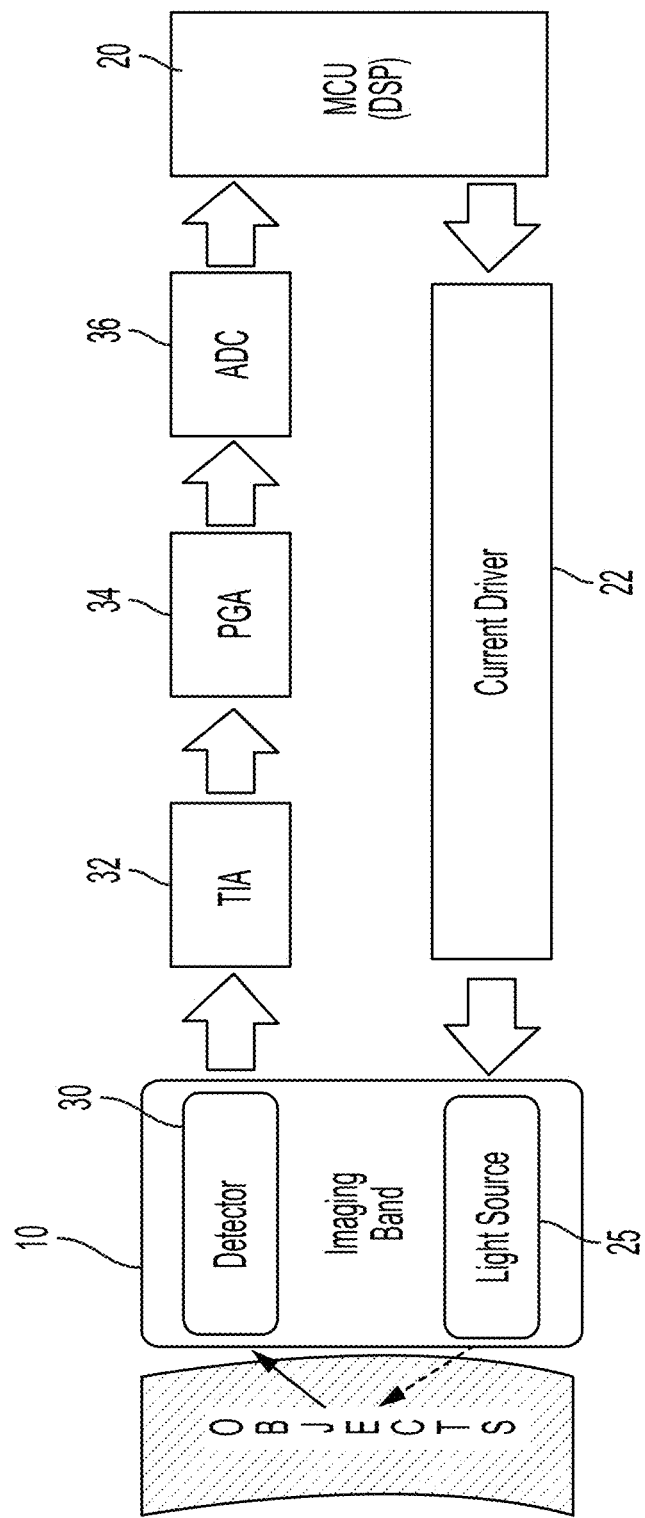
FIG. 2 depicts a block diagram for driving the light emitters and receiving inputs from the light detectors on the imaging bands.

FIG. 2 depicts a suitable block diagram for driving the light emitters 25 (e.g. LEDs or laser diodes) and receiving inputs from the light detectors 30 (e.g. photodiodes) on the imaging bands 10. One example of a suitable component for light delivery and light detection is the Osram SFH7050. The microcontroller 20 controls the current driver 22 that drives the LEDs 25. An example of a suitable driver for this purpose is the Texas Instrument TLC59711, and an example of a suitable microcontroller is the Microchip ATmega328. Optionally, the driver 22 may be configured to modulate the current that is applied to the LED 25 to produce modulated light, which can be advantageous for noise rejection purposes. In some embodiments, only one of the light emitters 25 is illuminated at any given instant. Light from the light emitter 25 will enter the subject's body. A suitable light intensity for this application is 2 mW/cm$^2$.

Some portion of the light will be reflected back towards some of the light detectors 30, while other portions of the illumination light may pass through tissue and be detected by other light detectors 30. Current from the photodiodes 30 is converted to voltage by transimpedance amplifiers 32 (e.g., with a gain of 20,000). In some preferred embodiments, one transimpedance amplifier 32 is provided for each of the photodiodes 30. The signal may be further amplified using a programmable gain amplifier (PGA) 34 to optimize the signal to the scale range of the analog to digital converter (ADC) 36 (e.g., a Texas Instrument ADS1115). The ADC digitizes the analog signal, and forwards the digitized data to the microcontroller 20. The signals received by the microcontroller 20 therefore represent light that has been reflected back towards some of the photodiodes 30 and also represent light that has been transmitted through the tissue to other ones of the photodiodes 30. The microcontroller 20 then determines the rise time and the plateau time of the transmissivity and reflectivity signals (as measured by the photodiodes 30 and reported to the microcontroller 20 via the ADC 36). Optionally, a low pass filter (not shown) may be added between the PGA 34 and the ADC 36 to remove noise from the signal.

Optionally, the microcontroller may be configured to transmit data to a mobile storage device (e.g. a smartphone, laptop, etc.) or another remote host (not shown). Optionally, absorption and reflectivity may be measured at more than one wavelength of light by obtaining signals from each of the photodetectors when the LEDs at each of the different wavelengths are activated.

In some preferred embodiments, only the detectors 30 in the light sources 25 are included in the imaging band that is positioned around the subject's fingers, and the remaining components 20-22 and 32-36 on a separate module (not shown). This separate module may be fabricated in the form of an additional flexible band that may be worn by the subject. Alternatively, this separate module may be fabricated in the form of a separate box or console.

To demonstrate the utility of this system for diagnosing SLE, a pilot study with 11 SLE patients with active arthritis and 4 healthy volunteers was performed. To image proximal interphalangeal (PIP) joints of the index-, middle-, and ring-fingers, two imaging bands 10 were wrapped around each joint and transmitted light intensities were gathered during blood pressure cuffs at 40 mmHg and 80 mmHg after both inflation and deflation. This resulted in 4-minute long hemodynamic time traces for all source-detector pairs. More specifically, Hemodynamic effects were obtained by inflating a pressure cuff first to 40 mmHg×60 seconds and then to 80 mmHg. Light at the 3 wavelengths (530, 655, 940 nm) was used to illuminate the PIP joints of the index-, middle-, and ring-fingers at 8 different points. Transmitted light intensities were measured with Si-photodetectors at 8 other positions (total 8×8×3=192 signal traces) starting just before the cuff inflation to 40 mmHg and ending 4 minutes later after deflation of the 80 mmHg cuff. Swollen, tender and healthy joints were examined by the same assessor.

Inflation of the cuff to either 40 mmHg or 80 mmHg induces a venous occlusion. Therefore, while the return of the blood to the heart is obstructed, arteries will still supply blood to the hand. This will lead to an increase of blood volume in the hand, which will increase absorption at all wavelengths and in turn leads to a decrease of light transmission. Upon deflation of the cuff, the blood will drain again from the hand and the optical transmission signals should increase to pre-cuff levels. Using diffuse optical imaging with continuous wave illumination allows for assessing the fast hemodynamic response to a venous occlusion.

Optical data was acquired throughout the cuff-experiment starting with a 60 seconds baseline measurement before the cuff was inflated. This was followed by a rapid inflation (<3 seconds), which was then held for another 60 seconds before the cuff was deflated. Measurements were continued for another 60 seconds to obtain a post-cuff baseline.

Once the raw data was recorded, it was processed for data analysis. To remove the noise occurring from electronics, respiration, and motion of objects, a discrete cosine transform (DCT) filter was applied to all traces. For the DCT filtering, two formulas referred to as the DCT and the inverse DCT (iDCT) were employed given by:

$$X_k = \sum_{n=0}^{N-1} x_n \cos\left(\frac{k\pi}{N}\left(n + \frac{1}{2}\right)\right), k = 0, 1, 2, \ldots, N-1 \quad \text{DCT}$$

$$y_k = \frac{1}{2}x_0 + \sum_{n=1}^{N-1} X_k \cos\left(\frac{n\pi}{N}\left(k + \frac{1}{2}\right)\right), k = 0, 1, 2, \ldots, K-1 \quad \text{iDCT}$$

Here $x_n$ is the input data for n points recorded and N is the number of data acquired during the cuff-experiment, which was 40. $y_K$ is the filtered signal and K is the total number of DCT coefficients that we considered for the filtering, which was 15. This DCT coefficient helped to generate filtered traces by removing high frequency signals, while maintaining shape of traces. Once all traces for all source-detector pairs were filtered, each trace was normalized based on the following equation:

$$S_{Norm}(k) = \frac{y(k) - \text{Min}(y(k))}{\text{Max}(y(k)) - \text{Min}(y(k))}$$

In this way, $S_{Norm}(k)$ varies between zero and one. In this way, the changes in the signal strength for each source-detector pair caused by the hemodynamic processes induced by the pressure cuff could be compared to each other.

Using the normalized traces, the overall hemodynamic response resulting from all source-detector pairs was considered. First, among a total of 192 (8×8×3) normalized traces, traces with an SNR below 10 dB were removed from the analysis. A mean trace extracted from all traces filtered and normalized was generated for each wavelength. The mean trace was reflected about x-axis and adjusted between 0 and 1 by the formula:

$$y(k) = -\frac{\sum_{i=0}^{n} S_{Norm}(i)}{n} + 1$$

As a result, a time-dependent signal was generated that shows a dynamic temporal response cause by the hemodynamic effects induced by the venous cuff. The maximum value is the highest point of blood pooling at the location where the imaging band 10 wrapped around while the pressure cuff was inflated. Therefore, this is the maximum time point of absorption by blood. For each wavelength, the standard deviation of the selected traces at a given time point were below ~0.3.

For these time-traces, two parameters, called the rise time ($t_R$) and the plateau time ($t_P$), were determined. The $t_R$ is determined by measuring the time it takes for the signal to rise to 90% of the largest value starting from 10% of the largest value. The $t_P$ is the time interval between points of 90% of the maximum from both the rising edge and falling edge.

RESULTS: SLE patients and normal controls dDOS data were available for analysis from 66 and 24 proximal interphalangeal (PIP) joints, respectively (PIPs 2-4). The recorded time traces typically showed an increase in total hemoglobin with the start of the cuff and a decrease with the release of the cuff. (see FIG. 3). From these traces, a rise, plateau, and fall time were calculated.

Figure 3:
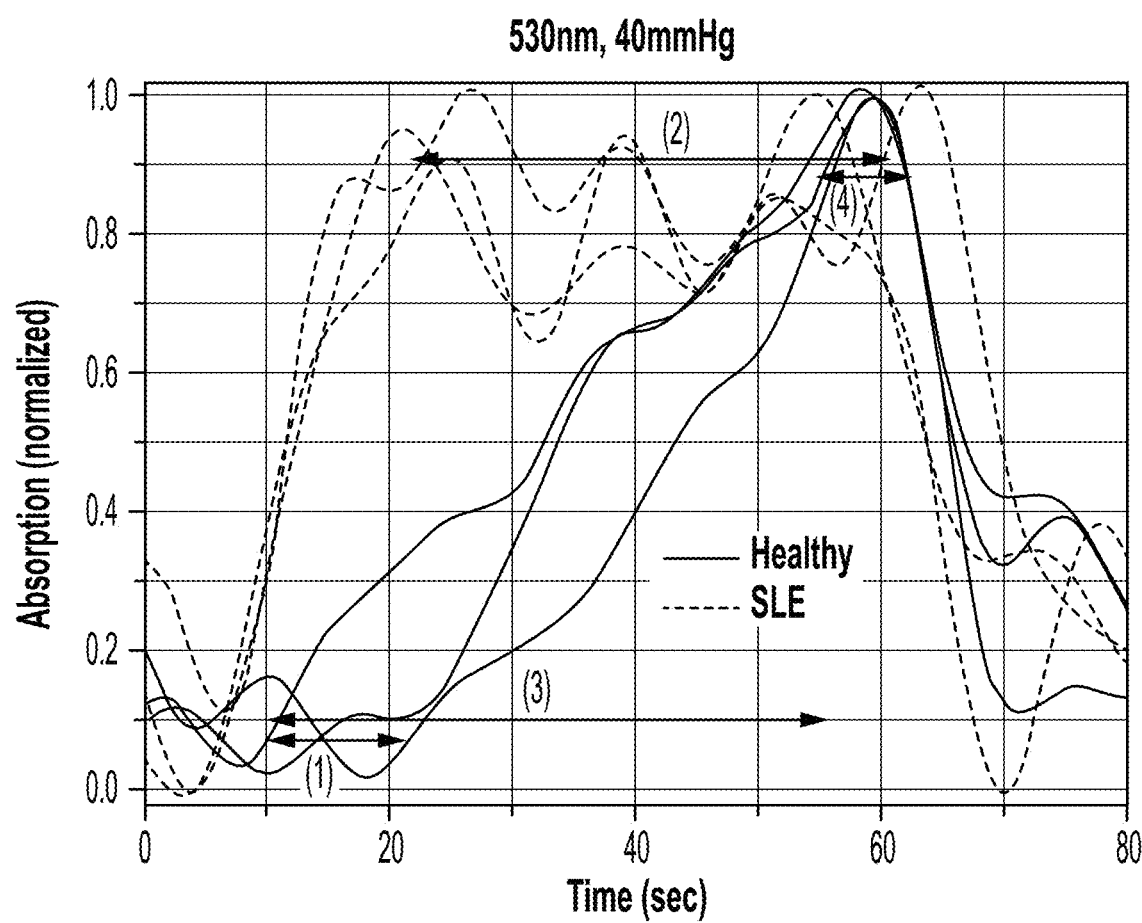
FIG. 3 depicts representative raw data for three healthy joints and three joints where SLE is present.

FIG. 3 depicts representative raw data for three finger joints of one healthy subject (solid lines) and three finger joints of one SLE arthritis subject (dashed lines). (1) and (2) are respectively the rise and the plateau times for a SLE patient, while (3) and (4) are respectively the rise and the plateau times for a healthy patient. It can be seen that SLE arthritis joints display a shorter rise time (time needed to increase from 10% to 90% of the maximum value) and a longer plateau time than healthy joints.

These experiments revealed that, on average, signals obtained from SLE patients displayed a shorter rise time and longer plateau time as compared to signals from healthy volunteers. Best results were obtained at λ=530 nm with cuff inflation at 40 mmHg. At those settings, the observed effects were very pronounced. These parameters may also be varied (e.g. λ between 500-560 nm; and inflation at 30-50 mmHg). Without being bound by this theory, one possible explanation for these results is that altered vessel physiology paired with already-increased blood pooling in the affected inflamed joints resulted in quicker increase in light absorption (rise time) that is maintained longer (plateau time) compared to normal joints. Similarly, without being bound by this theory, another possible explanation for this is that blood vessels in inflamed joints of SLE patients are stiffer and have a smaller capacity to expand. (Note that these two explanations are mutually consistent.)

Figure 4B:
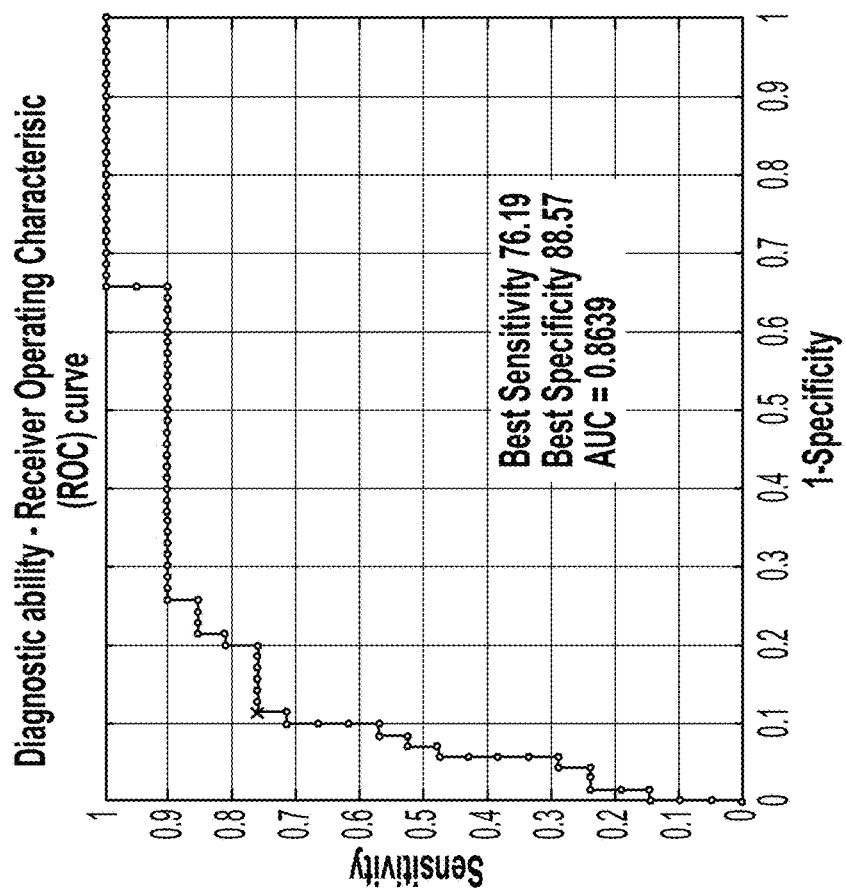
FIG. 4B depicts a 2-dimensional discriminant and ROC analysis on the rise and plateau times.
Figure 4A:
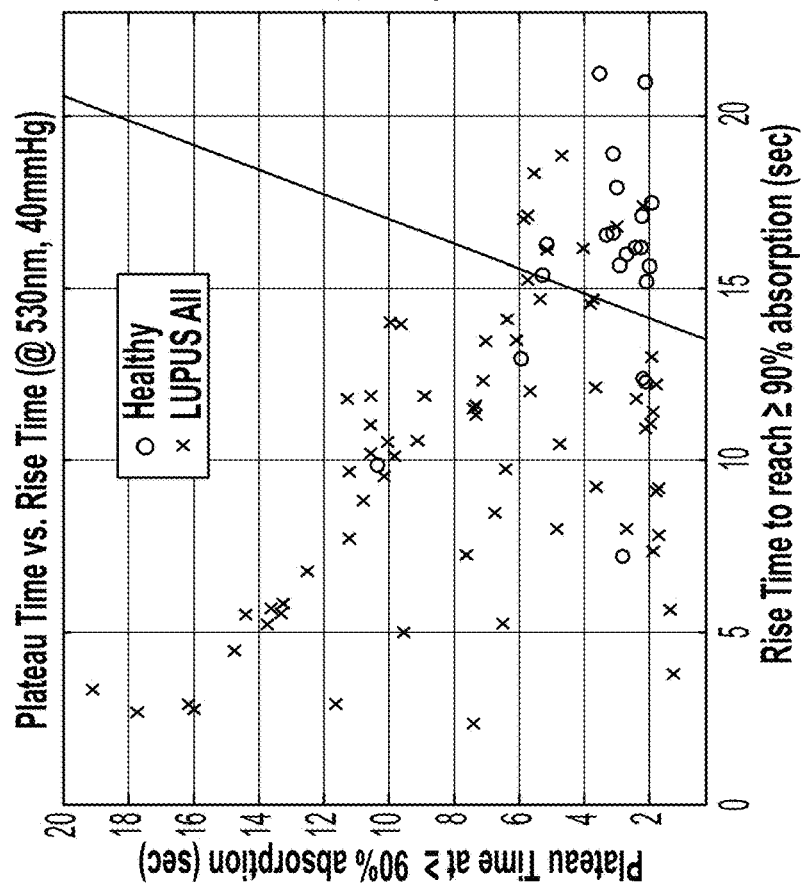
FIG. 4A depicts the data for a 2-dimensional discriminant plot of healthy patients and SLE patients.

FIG. 4A depicts the raw data for a 2-dimensional discriminant plot of healthy patients (o) and lupus patients (x), plotting the rise time (in seconds) to reach greater than or equal to 90% absorption on the x-axis, and the plateau time (in seconds) at greater than or equal to 90% absorption on the y-axis. As seen in FIG. 4B, performing a 2-dimensional discriminant and ROC analysis on the rise and plateau times, it was possible to achieve specificity of 88.57% with a sensitivity of 76.19% (AUC=0.8639) when taking into account the rise time and the plateau time of the absorption signals. These results are consistent with excellent discrimination.

Figure 5:
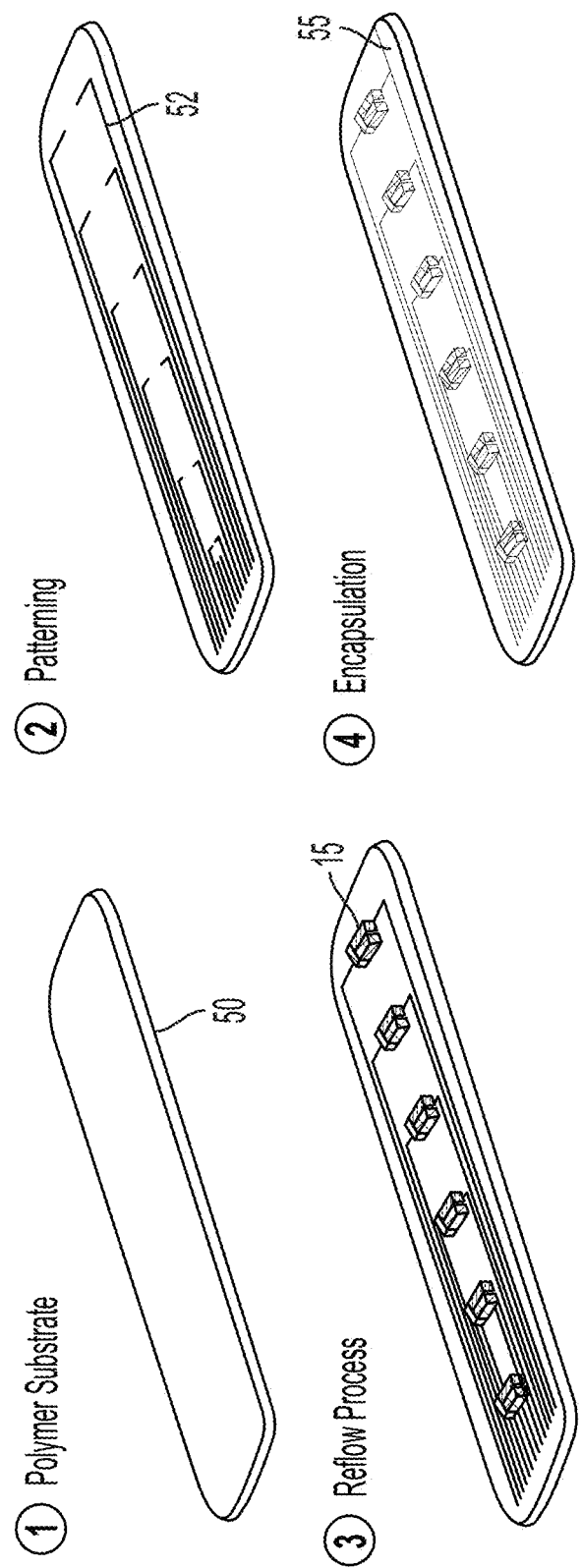
FIG. 5 depicts the steps of one suitable process for fabricating the imaging bands.

FIG. 5 depicts the steps of one suitable process for fabricating the imaging bands 10. In step 1, a polymer substrate 50 (e.g., polyimide) is deposited. In step 2, conductive traces 52 (e.g., copper traces) are added to the polymer substrate 50 (e.g., using a lithography process). In step 3 the light emitters (e.g., LEDs) and light detectors (e.g. photodiodes), which are included within modules 15, are connected to the conductive traces 52 (e.g., using a reflow process). In step 4, encapsulation 55 is preferably provided to even out the surface of the band that will contact the patient's skin to improve attachments and provide protection for the optical components. This may be implemented, for example by depositing parylene by chemical vapor deposition (CVD) to cover the exposed electrodes.

These results show that dDOS can evaluate SLE arthritis with high sensitivity and specificity. Rise and plateau time of the optical traces correlate strongly with swollen and tender joint count. The advantages of dDOS are non-invasiveness, objectivity (eliminating inter-rater variability and operator dependency), low cost, and high speed of performance (~5 min per area of scanning) compared to ultrasound and MRI. dDOS has the potential to bring much-needed objectivity to the quantification of SLE arthritis.

The system described herein enables localized waveform/image-based diagnosis with low-cost in daily life. Because of the low costs and ease of handling, it has the potential to become a versatile point-of-care tool.

In addition to the assessing the hemodynamic trace analysis, the hardware described above can also be used to perform tomographic image reconstruction and generate 3-dimensional maps of total hemoglobin concentrations in the relevant joints. The time trace data was used as input to the image reconstruction code to obtain three-dimensional maps of hemodynamics (i.e., dynamic changes in total hemoglobin (tHb) concentration and tissue oxygenation) in the finger. Dynamic tomographic reconstruction was performed using a partial differential equation (PDE)-constrained reduced-space sequential quadratic programming (rSQP) method. Starting with an estimate of the baseline hemoglobin concentration, the dynamic rSQP method reconstructs the time-varying 3D map of chromophores sequentially, sweeping through all subsequent time points by making use of the previous time point result as a new initial guess for the next time-point reconstruction.

The equation of radiative transfer (ERT) has been used here as a light propagation model since the ERT can provide better predictions of light-tissue interactions in the finger tissue that constitutes small tissue volume and void-like region (i.e., synovial fluid). Discrete cosine transformation (DCT) were used to compress tomographic images with a few DCT coefficients, which leads to a much efficient and better conditioned inverse problem where only a small number of DCT coefficients are to be found with the minimization procedure.

Three-dimensional volumetric PIP finger meshes are generated from surface meshes obtained with the laser scanner (DAVID Laserscanner) as developed in the previous work. A typical 3D volume mesh was composed of approximately 42000 tetrahedron elements.

Figure 6:
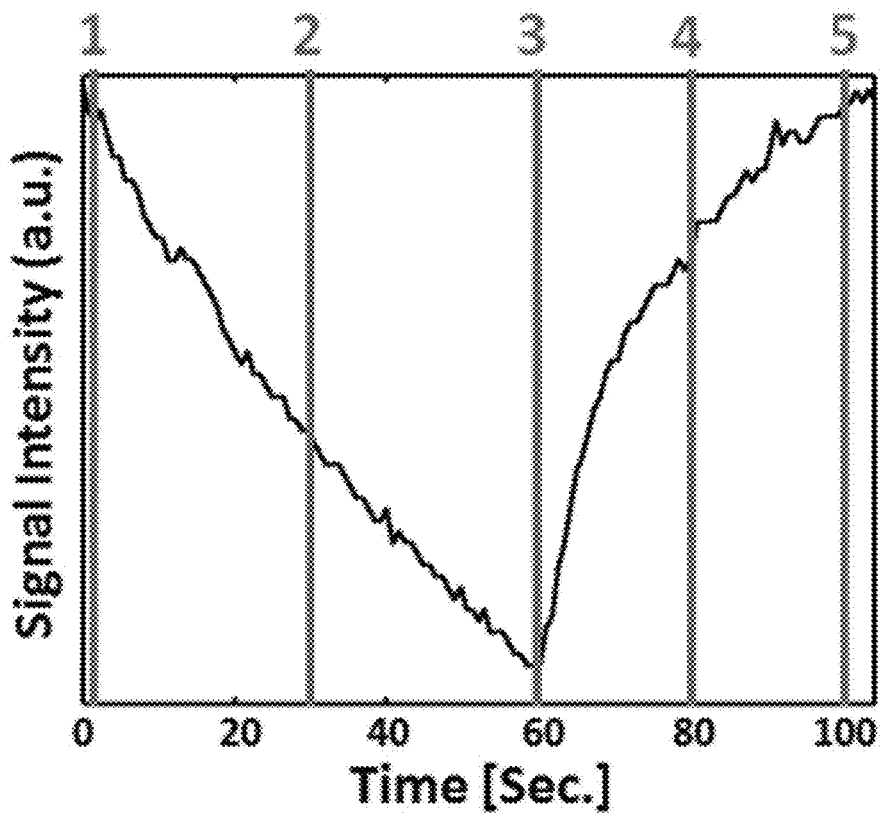
FIG. 6 shows raw signal response to venous occlusion of 40 mmHg placed on forearm.
Figure 7:
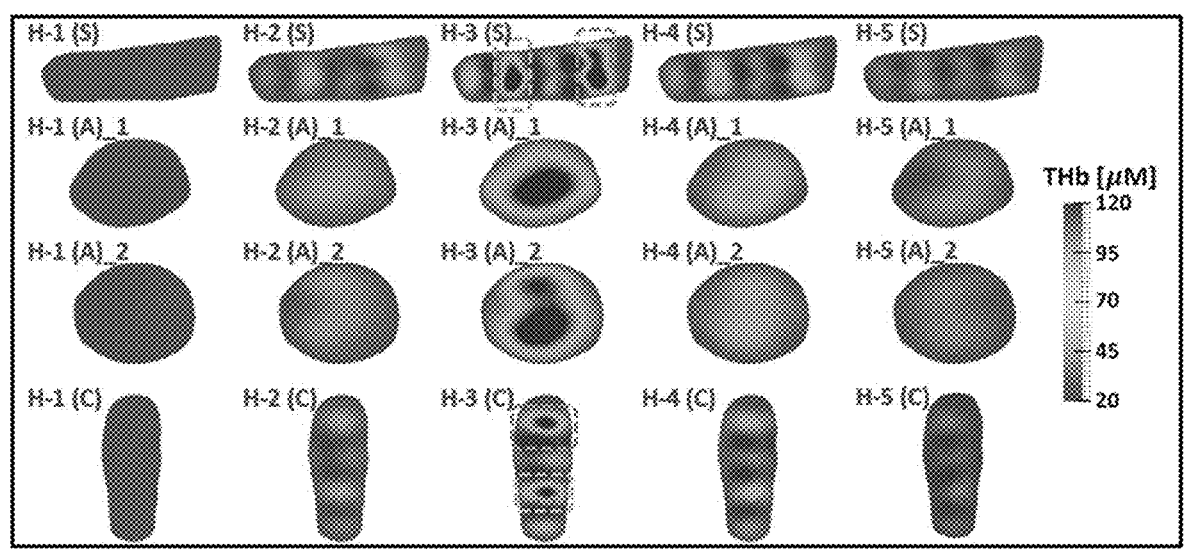
FIG. 7 depicts cross-sectional images of THb concentration from a healthy finger.
Figure 8:
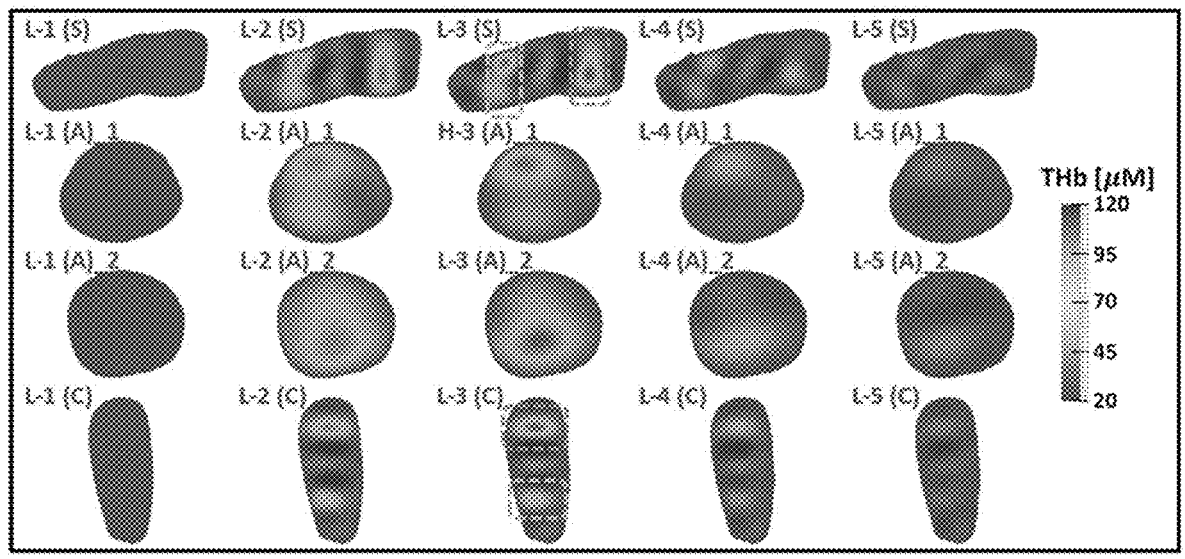
FIG. 8 depicts cross-sectional images of THb concentration from a SLE finger.
Figure 9:
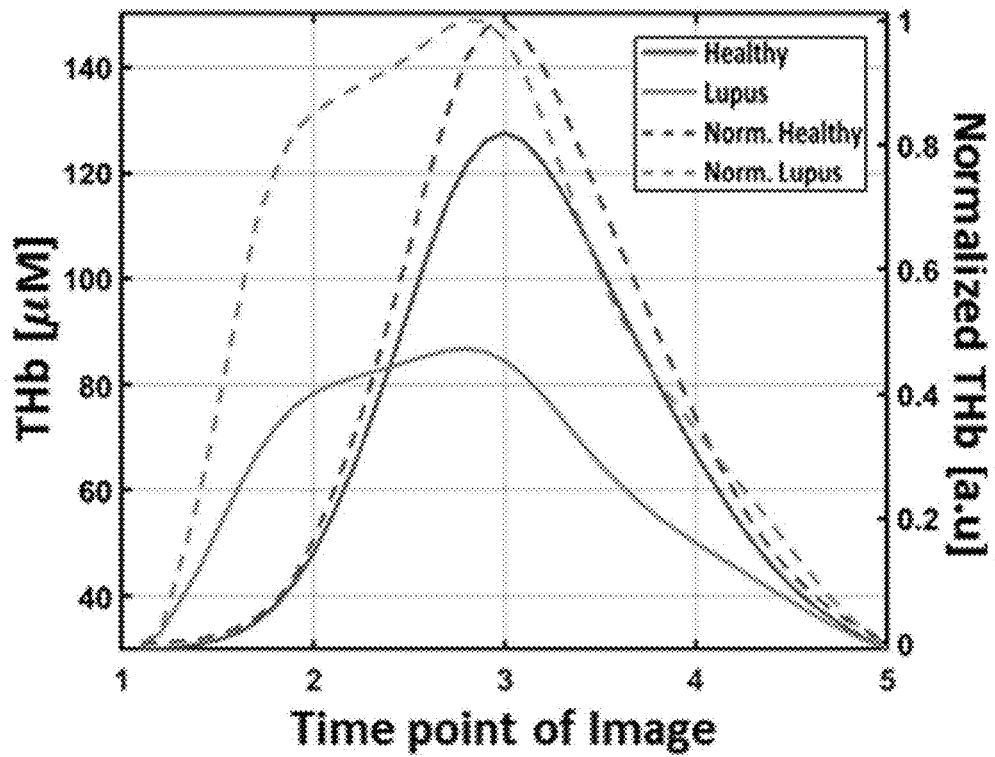
FIG. 9 is a graph depicting changes of average THb and normalized THb in a ROI for each time point for both healthy and SLE fingers.

In one experiment, for each finger of each of the subjects a total of 40 such volumetric maps (one per two seconds) were generated, and FIGS. 6-9 show a subset of the results. These figures show the concentration of total hemoglobin (THb): cross-sectional finger images based on anatomical planes (S: Sagittal, A: Axial, C: Coronal) at different time points. More specifically, FIG. 6 shows raw signal response to venous occlusion of 40 mmHg placed on forearm. The five vertical lines indicate the five different time points for which representative reconstructions are shown in FIGS. 7 and 8. Those five time points are as follows: just before the cuff inflation (1), one time point in the middle of the inflation (2), one time point just before the release of the cuff (3), another point 20 seconds after the release of the cuff (4) and final time point 100-seconds after the release of the cuff, when the transmitted light signal reached a level comparable to the intensity at the beginning of the cuff experiment (5).

Cross-sectional images of THb concentration from a healthy finger (FIG. 7) and from a SLE finger (FIG. 8) were generated. The two regions where the flexible bands 10 were wrapped around are shown as dotted boxes at the tip side of finger the base side of the finger. In both FIG. 7 and FIG. 8, the top rows show 5 sagittal cross-section of total hemoglobin (THb). The second and third rows show axial cuts at the tip side of finger and at the base side of finger, respectively. Two axial planes correspond to the positions where two imaging bands 10 were wrapped around. The bottom rows show coronal cuts.

Looking at the cross-sectional images of the finger of the healthy subject, one can observe an increase in THb in certain regions of the finger from the beginning of the cuff until the time point 3, when the pressure cuff is released. After the release the THb reverts to pre-cuff levels. In general, this behavior is very similar to what was observed in the raw traces discussed above in connection with FIG. 3. However, while the raw traces are averaged over the entire finger, these 3-dimensional images show the location of these changes inside the finger.

To study the temporal responses, a region of interest (ROI) was defined as area where the THb concentration is above 50% of the maximum value of THb concentration. For both fingers of healthy subject and SLE patient, this ROI successfully represents the particular area where THb concentration changes inside green-dotted boxes and bluedotted boxes (See. FIGS. 7 and 8). Integrating over the values inside the ROI at each time point, results in a time trace seen in FIG. 9, which depicts the changes of average THb (straight lines) at the given volume and normalized THb (dashed lines) for each time point between a healthy finger (traces 92, 94) and a SLE finger (traces 96, 98).

Compared to the results obtained with the healthy finger, THb values in images of the fingers of SLE patients are smaller. Applying the same ROI analysis as in the finger of the healthy control and SLE patient, a hemodynamic response curve was derived. In addition to the amplitude difference, differences in the rise and plateau times were observed, which correspond to the trace analysis discussed above. Furthermore, it appears that the fall time (or speed of outflow) is slower. This effect was not visible from the hemodynamic trace analysis discussed above in connection with FIG. 3, perhaps because it may have been averaged out. Overall, the results show that the imaging bands can distinguish a healthy finger from an SLE finger in terms of hemodynamic changes with tomographic imaging techniques.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An imaging system comprising:
a flexible substrate;
a plurality of light-emitting diodes (LEDs) positioned on the flexible substrate at intervals along the flexible substrate, wherein the LEDs are positioned with respect to the flexible substrate to couple light into a finger of a subject;
a plurality of photodetectors positioned on the flexible substrate at intervals along the flexible substrate, wherein the LEDs are positioned with respect to the flexible substrate to detect light emanating from the finger;
a controller; and
a plurality of LED drivers configured to selectively illuminate each of the LEDs of the plurality of LEDs in response to receipt of a command from the controller,
wherein the controller accepts an output from each of the photodetectors of the plurality of photodetectors, and determines, from each output from each of the photodetectors, a level of light absorption or transmission within the finger,
wherein the plurality of LEDs and the plurality of photodetectors are configured to be affixed against the subject's body near a joint, and
wherein the controller is configured to:
(a) sequentially transmit light from each of the plurality of LEDs into the subject's body;
(b) acquire signals from each of the plurality of photodetectors, wherein the signals represent an amount of light that reaches each of the plurality of photodetectors during a time when each of the plurality of LEDs is transmitting light into the subject's body;
(c) determine a rise time of the acquired signals that occurs in response to an increase of blood volume that results from an inflation of a pressure cuff, wherein the inflation of the pressure cuff occurs between a start time, wherein the rise time is determined by measuring the time it takes for the acquired signals to rise to 90% of a largest value starting from 10% of the largest value and a stop time; and
(d) determine a plateau time of the acquired signals that occurs in response to the increase of blood volume and a subsequent decrease of blood volume that results from the inflation and subsequent deflation of the pressure cuff, wherein the plateau time is determined by measuring a time interval between points of 90% of a maximum from both a rising edge and a falling edge of the acquired signals, and
wherein the controller is further configured to output an indication that the joint is likely affected by systemic lupus erythematosus (SLE) when the determined rise time is short and the determined plateau time is long.

2. The imaging system of claim 1, wherein the controller is configured to output an indication that the joint is likely not affected by SLE when the determined rise time is long and the determined plateau time is short.

3. The imaging system of claim 1, wherein the controller is configured to output the indication that the joint is likely affected by SLE when the determined rise time is less than 20 seconds and the determined plateau time is long.

4. The imaging system of claim 1, wherein the controller is configured to output an indication that the joint is likely not affected by SLE when the determined rise time is more than 40 seconds.

5. The imaging system of claim 1, wherein the pressure cuff is inflated to between 30 mmHg and 50 mmHg.

6. The imaging system of claim 1, wherein the stop time is at least 60 seconds after the start time.

7. The imaging system of claim 1, wherein the plurality of LEDs and the plurality of photodetectors are adapted to be held against the subject's body near the joint using the flexible substrate.

8. The imaging system of claim 1, wherein the plurality of LEDs and the plurality of photodetectors are arranged in a plurality of modules, with each of the modules including at least one LED and at least one photodetector.

9. The imaging system of claim 1, wherein the plurality of LEDs emit light with a wavelength between 500 nm and 560 nm.

10. The imaging system of claim 1, wherein the flexible substrate comprises a flex circuit.

11. The imaging system of claim 1, wherein the flexible substrate comprises a polyimide layer with a plurality of conductive traces disposed on the polyimide layer.

12. The imaging system of claim 1, further comprising a plurality of transimpedance amplifiers, wherein each of the transimpedance amplifiers is configured to amplify an output of a respective one of the photodetectors of the plurality of photodetectors.

13. The imaging system of claim 12, further comprising an analog-to-digital converter configured to digitize outputs of the transimpedance amplifiers and forward corresponding data to the controller.

14. The imaging system of claim 1, further comprising the pressure cuff.

15. A method of diagnosing systemic lupus erythematosus (SLE) in a subject, the method comprising:
(a) providing an imaging system comprising:
a flexible substrate;
a plurality of light emitting diodes (LEDs) positioned on the flexible substrate at intervals along the flexible substrate, wherein the LEDs are positioned with respect to the flexible substrate to couple light into a finger of a subject;

a plurality of photodetectors positioned on the flexible substrate at intervals along the flexible substrate, wherein the LEDs are positioned with respect to the flexible substrate to detect light emanating from the finger;

a controller; and a plurality of LED drivers configured to selectively illuminate each of the LEDs in response to receipt of a command from the controller, wherein the controller accepts an output from each of the photodetectors, and determines, from each output from each of the photodetectors, a level of light absorption or transmission within the finger;

(b) affixing the plurality of LEDs and the plurality of photodetectors against the subject's body near a joint;

(c) sequentially transmitting light from each of the plurality of LEDs into the subject's body; and (d) acquiring signals from each of the plurality of photodetectors, wherein the signals represent an amount of light that reaches each of the plurality of photodetectors during a time when each of the plurality of LEDs is transmitting light into the subject's body;

(e) determining a rise time of the acquired signals that occurs in response to an increase of blood volume that results from an inflation of a pressure cuff, wherein the inflation of the pressure cuff occurs between a start time and a stop time, wherein the rise time is determined by measuring the time it takes for the acquired signals to rise to 90% of a largest value starting from 10% of the largest value;

(f) determining a plateau time of the acquired signals that occurs in response to the increase of blood volume and a subsequent decrease of blood volume that results from the inflation and subsequent deflation of the pressure cuff, wherein the plateau time is determined by measuring a time interval between points of 90% of a maximum from both a rising edge and a falling edge of the acquired signals; and (e) outputting an indication that the joint is likely affected by SLE when the determined rise time is short and the determined plateau time is long.

* * * * *